United States Patent [19]

Benn

[11] 4,062,843

[45] Dec. 13, 1977

[54] 23-HYDROXY-3-OXO-24-NORCHOLA-4,17(20)-DIEN-21-OIC ACID γ-LACTONE AND INTERMEDIATES THERETO

[75] Inventor: Walter R. Benn, Deerfield, Ill.

[73] Assignee: G. D. Searle & Co., Chicago, Ill.

[21] Appl. No.: 755,306

[22] Filed: Dec. 29, 1976

[51] Int. Cl.$^2$ ............ C07J 71/00; C07J 9/00; C07J 17/00

[52] U.S. Cl. ............ 260/239.55 R; 260/397.1; 260/239.57

[58] Field of Search .................. 260/239.57

[56] References Cited

U.S. PATENT DOCUMENTS 3,707,537   12/1972   Kierstead et al. ............ 260/239.55 C

*Primary Examiner*—Elbert L. Roberts
*Attorney, Agent, or Firm*—John M. Brown

[57] ABSTRACT

23-Hydroxy-3-oxo-24-norchola-4,17(20)-dien-21-oic acid γ-lactone, intermediates thereto, and antiviral utility thereof are disclosed.

7 Claims, No Drawings

23-HYDROXY-3-OXO-24-NORCHOLA-4,17(20)-DIEN-21-OIC ACID γ-LACTONE AND INTERMEDIATES THERETO

The invention relates to 23-hydroxy-3-oxo-24-norchola-4,17(20)-dien-21-oic acid γ-lactone, intermediates thereto, and processes for the preparation thereof. More particularly, this invention provides a new, useful, and unobvious antiviral agent having the formula

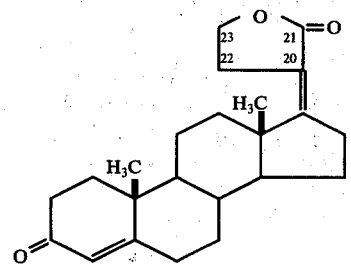

the antiviral utility of which is evident from the results of a standardized test for its capacity to inhibit the growth of influenza type A virus (strain 575). In this test, cell cultures of primary rhesus monkey kidney maintained in 25-ml plastic flasks each containing test compound in concentrations of 625, 125, 25, 5, or 1 mcgm/ml are prepared in pairs. These flasks, and an identical pair of flasks containing no test compound, are each inoculated with a dose of influenza type A virus (strain 575) previously known to produce maximum hemadsorption and minimum cytopathogenic effects after a 24-hour incubation. Where the cultures contain test compound, the virus is added 1 hour after addition of the compound to the culture. Following a 24-hour incubation of the cultures, the supernatant fluids are removed and 3.0 ml of a 0.4 percent suspension of guinea pig erythrocytes is added to each flask. The flasks are then incubated at 4° C in a horizontal position for 30 minutes. The flasks are rocked every 10 minutes during the incubation period. After this incubation, the red cell suspension is decanted from each flask, the flasks are washed twice with 3.0 ml of phosphate buffer solution(pH 7.4) to remove unadsorbed red cells, and 3.0 ml of distilled water is then added to lyse the adsorbed cells. The flasks are further incubated at 37° C for 30 minutes in a horizontal position and rocked every 10 minutes. After this incubation, the fluid contents of the pairs of flasks are combined to form an assay unit and maintained at room temperature for 15–30 minutes to allow settling of cellular debris. A pair of control flasks identical with the above except for the absence of test compound and virus inoculation, is run concurrently. The optical density of the resultant hemoglobin solutions is determined via a Beckman spectrophotometer at about 415 millimicrons. A test compound is considered active if, at one of the tested levels, it reduces the optical density by at least 50%, relative to the virus control. 23-Hydroxy-3-oxo-24-norchola-4,17(20)-dien-21-oic acid γ-lactone was found active at 275 mcgm/ml in this test. The well-known antiviral agent, amantadine hydrochloride, was found active at 0.69 mcgm/ml in this test.

Those skilled in the art will recognize that observations of activity in standardized tests for particular biological effects are fundamental to the development of valuable new drugs, both veterinary and human.

23-Hydroxy-3-oxo-24-norchola-4,17(20)-dien-21-oic acid γ-lactone can be prepared by heating a solution of 3β,17-dihydroxy-17α-pregna-5,20-diene-21-carboxylic acid γ-lactone (U.S. Pat. No. 2,705,712) in sulfinylbismethane with sodium cyanide; acidifying an aqueous solution of the resultant sodium 20-cyano-3β-hydroxypregna-5,17(20)-diene-21-carboxylate; esterifying, selectively hydrolyzing, and cyclodehydrating the resultant 20-cyano-3β-hydroxypregna-5,17(20)-diene-21-carboxylic acid by heating it with formic acid; reducing the 23-carbonyl to methylene in the resultant 3β-(formyloxy)-21-oxo-14α-carda-5,17(20)-dienolide by contacting the dienolide with sodium tetrahydroborate (1-) in tetrahydrofuran solution, then heating the reaction product with aqueous bicarbonate in methanol to complete hydrolysis of the exocyclic ester group initiated by the tetrahydroborate; and, finally, subjecting the resultant 3β,23-dihydroxy-5,17(20)-dien-21-oic acid γ-lactone to Oppenauer oxidation, Alternatively, 20-cyano-3β-hydroxypregna-5,17(20)-diene-21-carboxylic acid can be esterified, selectively hydrolyzed, and cyclodehydrated by contacting it with boron fluoride in a mixture of acetic acid and acetic anhydride; the 23-carbonyl can be reduced to methylene in the resultant 3β-(acetyloxy)-21-oxo-14α-carda-5,17(20)-dienolide by contacting the dienolide with sodium tetrahydroborate (1-) in tetrahydrofuran solution; the exocyclic ester group in the resulting 3β-(acetyloxy)-23-hydroxy-24-norchola-5,17(20)-dien-21-oic acid γ-lactone can be hydrolyzed by heating the lactone with aqueous carbonate in methanol; and the resultant 3β,23-dihydroxy-24-norchola-5,17(20)-dien-21-oic acid γ-lactone can be converted to 23-hydroxy-3-oxo-24-norchola-4,17(20)-dien-21-oic acid γ-lactone, as remarked above, via Oppenauer oxidation.

Still another route to 23-hydroxy-3-oxo-24-norchola-4,17(20)-dien-21-oic acid γ-lactone is as follows: 17-Hydroxy-3-oxo-17α-pregna-4,20-diene-21-carboxylic acid γ-lactone (U.S. Pat. No. 2,705,712) is heated with sodium cyanide in sulfinylbismethane to produce sodium 20-cyano-3-oxopregna-4,17(20)-diene-21-carboxylate. Acidification of this salt affords the corresponding acid, which is esterified, selectively hydrolyzed, and cyclodehydrated by heating it with formic acid. The resultant 3,21-dioxo-14α-carda-4,17(20)-dienolide is selectively reduced by contacting it with sodium tetrahydroborate(1-) in tetrahydrofuran; and the 3,23-dihydroxy-24-norchola-4,17(20)-dien-21-oic acid γ-lactone which eventuates is oxidized to the corresponding 3-one by contacting it with (a) manganese oxide in chloroform solution or (b) a suspension of silver carbonate-impregnated diatomaceous earth in a solvent such as benzene, 2-propanone, or methanol.

Among the foregoing intermediates, 3β-(acetyloxy)-23-hydroxy-24-norchola-5,17(20)-dien-21-oic acid γ-lactone is additionally valuable in that, like 23-hydroxy-3-oxo-24-norchola-4,17(20)-dien-21-oic γ-lactone, it is an antiviral agent. In the standardized test for activity vis-a-vis influenza A virus (strain 575) hereinbefore detailed, 3β-(acetyloxy)-23-hydroxy-24-norchola-5,17(20)-dien-21-oic acid γ-lactone was found active at 24 mcgm/ml; and in a test identical therewith excepting that the virus employed is influenza B virus (strain MB), the compound was found active at 18 mcgm/ml.

Further evidence of the antiviral activity of 3β-(acetyloxy)-23-hydroxy-24-norchola-5,17(20)-dien-21-oic acid γ-lactone is provided by the results of a standardized test for its capacity to inhibit the growth of vesicular stomatitis virus (strain Indiana) and poliomyelitis type I virus (strain Sabin). In the former test, monolayer cell cultures of primary cynomologus monkey kidney are established in multi-dish plates, each plate consisting of six 6 × 34-mm wells. After cell outgrowth, the nutrient fluids are removed from the wells and the cell sheets are inoculated with 0.25 ml of a dilution of vesicular stomatitis virus (Indiana) previously shown to cause confluent lysis of the cell sheets. After a virus absorption period of 1-1½ hours, the inoculum is removed by aspiration; and 2.0 ml of an agar overlay containing neutral red is then added and allowed to solidify, whereupon a ¼-inch paper disc — previously impregnated with 0.02 ml of a 10 mg/ml solution of test compound in water or a suitable organic solvent and allowed to dry — is placed onto the center of the agar surface of each well. The plates are incubated at 37° C for 4 days, at the end of which time they are examined for zones of cytotoxicity and antiviral inhibition. The diameter of the antiviral zone divided by the diameter of the cytotoxic zone must amount to at least 1.5 to qualify a compound as active in this test. For 3β-(acetyloxy)-23-hydroxy-24-norchola-5,17(20)-dien-21-oic acid γ-lactone, this value is found to be 14.5. For the well-known antiviral agent, mycophenolic acid, the value is found to be 11.0.

In a test identical with that for activity vis-a-vis vesicular stomatitis virus (strain Indiana) above, excepting that (1) the virus employed is poliomyelitis type I virus (strain Sabin), (2) either cynomologus or rhesus monkey kidney is used to establish the monolayer cell cultures called for, and (3) the diameter of the antiviral zone divided by the diameter of the cytotoxic zone must amount to at least 5.0 to qualify a compound as active, this value for 3β-(acetyloxy)-23-hydroxy-24-norchola-5,17(20)-dien-21-oic acid γ-lactone was found to be 15.5.

The following examples describe in detail various processes for preparing 23-hydroxy-3-oxo-24-norchola-4,17(20)-dien-21-oic acid γ-lactone. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a slurry of 200 parts of 3β,17-dihydroxy-17α-pregna-5,20-diene-21-carboxylic acid γ-lactone in approximately 1400 parts of sulfinylbismethane at 70° is added, with stirring, 34 parts of sodium cyanide. Stirring at 70° is continued for approximately 4 hours, during which time solution occurs within a few minutes and a heavy precipitate is formed after about 1 hour. Following the heating period, the reaction mixture is cooled, whereupon insoluble solids are separated therefrom by filtration, consecutively washed with sulfinylbismethane and 1,1'-oxybisethane, and recrystallized from methanol to give sodium 20-cyano-3β-hydroxypregna-5,17(20)-diene-21-carboxylate melting at 293°–297°. The product has the formula

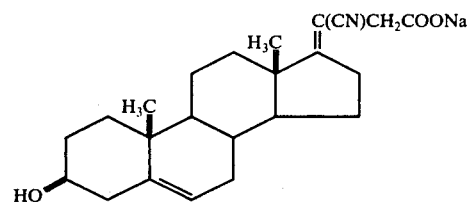

B. A solution of 20 parts of sodium 20-cyano-3β-hydroxypregna-5,17(20)-diene-21-carboxylate in 1000 parts of warm water is acidified with 100 parts of 4% hydrochloric acid. Approximately 1 hour later, the precipitate which has formed is separated by filtration, washed with water, dried in vacuo, and recrystallized from methanol to give 20-cyano-3β-hydroxypregna-5,17(20)-diene-21-carboxylic acid melting at 245°–250°. The product has the formula

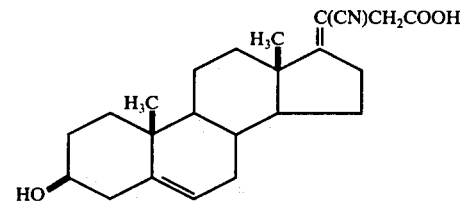

C. A solution of 10 parts of 20-cyano-3β-hydroxypregna-5,17(20)-diene-21-carboxylic acid in approximately 520 parts of 98% formic acid is heated at the boiling point under reflux — protected from moisture — for about 2 hours, whereupon the reaction mixture is distilled to dryness in vacuo. The residue is taken up in 10 volumes of benzene; and the benzene solution is consecutively washed with cold water, aqueous 5% sodium bicarbonate, and aqueous 55% sodium chloride, then dried over anhydrous sodium sulfate and finally stripped of solvent by vacuum distillation. The residual yellow solid, recrystallized from acetone or ethyl acetate, affords 3β-(formyloxy)-21-oxo-14α-carda-5,17(20)-dienolide melting at 215°–218°. The product has the formula

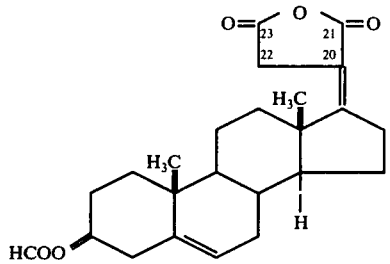

D. To a cold solution of 20 parts of sodium tetrahydroborate(1-) in 900 parts of tetrahydrofuran is slowly added, with stirring, a solution of 105 parts of 3β-(formyloxy)-21-oxo-14α-carda-5,17(20)-dienolide in 1800 parts of tetrahydrofuran. The resultant mixture is stirred at room temperatures for 4 hours, whereupon 2150 parts of 15% hydrochloric acid is introduced and the mixture thus obtained concentrated to approximately ⅓th of its original volume by vacuum distillation. The distilland is cooled and then extracted with trichloromethane. The trichloromethane extract is washed with aqueous 15% sodium chloride, dried over anhydrous sodium sulfate, and stripped of solvent by vacuum distillation. To the residue is added approximately 150 parts of aqueous 8% sodium bicarbonate and 1600 parts of methanol. The resultant mixture is heated at the boiling point under reflux for ½ hour, then concentrated to ⅓rd of its original volume by distillation. The distilland is acidified with 5% hydrochloric acid, and the mixture thus obtained is poured into 5 volumes of water. Insoluble solids are filtered out, dried in air, and recrystallized from aqueous methanol to give 3β,23-dihydroxy-24-norchola-5,17(20)-dien-21-oic acid γ-lactone as a colorless solid. The product has the formula

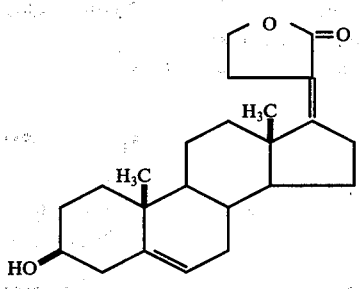

E. From a solution of 15 parts of 3β,23-dihydroxy-24-norchola-5,17(20)-dien-21-oic acid γ-lactone and 75 parts of cyclohexanone in 520 parts of toluene, approximately 1/10th of the volume is distilled off, whereupon the distilland is cooled and 15 parts of aluminum isopropoxide added thereto. The resultant mixture is concentrated by distillation to approximately ⅓rd of its original volume during 1½ hours, at which point the distilland is cooled and diluted with approximately 70 parts of a saturated aqueous solution of Rochelle salt. The mixture thus obtained is subjected to steam distillation. When the distillate amounts to approximately 5000 parts of liquid, distillation is stopped, the distilland is cooled, and liquid is removed from the solids precipitated therein by decantation. The solids are taken up in dichloromethane, and the dichloromethane solution is consecutively washed with water and aqueous 35% sodium chloride, then filtered through diatomaceous earth. The filtrate is dried over anhydrous sodium sulfate and stripped of solvent by vacuum distillation. The residue, a viscous syrup, crystallizes on trituration with 2-propanone. The crystalline material is separated by filtration and recrystallized from a mixture of 2-propanone and methylcyclohexane to give 23-hydroxy-3-oxo-24-norchola-4,17(20)-dien-21-oic acid γ-lactone melting at 226°-229.5°. The product has the formula

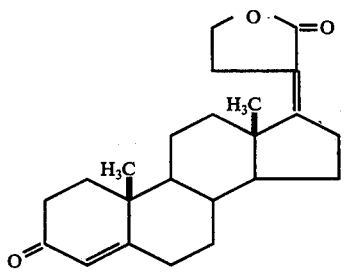

EXAMPLE 2

A. A solution of 19 parts of 20-cyano-3β-hydroxypregna-5,17(20)-diene-21-carboxylic acid and 9 parts of boron fluoride-diacetic acid complex in a mixture of 28 parts of acetic anhydride and 1600 parts of acetic acid is stirred at room temperatures for 20 hours, whereupon 10 parts of water is introduced and the resultant mixture is concentrated to approximately ⅓rd of its original volume by vacuum distillation at 60°-65° during 4 hours. The distilland is filtered, and the filtrate is poured into 2000 parts of water. Insoluble solids are filtered out, dried in air, and recrystallized from 2-propanone to give 3β-(acetyloxy)-21-oxo-14α-carda-5,17(20)-dienolide melting at 242°-250°.

B. To a slurry of 4 parts of sodium tetrahydroborate(1-) in 90 parts of tetrahydrofuran at 0°-5° is added, with stirring during approximately 15 minutes, a solution of 20 parts of 3β-(acetyloxy)-21-oxo-14α-carda-5,17(20)-dienolide in 355 parts of tetrahydrofuran. The resultant mixture is stirred at room temperatures for 3 hours, whereupon 55 parts of 15% hydrochloric acid is introduced. The mixture thus obtained is concentrated to approximately half of its original volume by vacuum distillation, and the distilland is poured into 2000 parts of water. The gummy product which precipitates is extracted with trichloromethane. The trichloromethane solution is consecutively washed with water and aqueous 35% sodium chloride, dried over anhydrous sodium sulfate, and stripped of solvent by vacuum distillation. The residue is dissolved in 1,1'-oxybisethane. This solution is consecutively washed with 4% hydrochloric acid, aqueous 5% sodium bicarbonate, and aqueous 35% sodium chloride, then dried over anhydrous sodium sulfate, and finally stripped of solvent by vacuum distillation. The residue is 3β-(acetyloxy)-23-hydroxy-24-norchola-5,17(20)-dien-21-oic acid γ-lactone which can be further purified by crystallization from 2-propanone.

C. A mixture of 3 parts of 3β-(acetyloxy)-23-hydroxy-24-norchola-5,17(20)-dien-21-oic acid γ-lactone, 10 parts of a saturated aqueous solution of sodium carbonate, and 80 parts of methanol is heated at the boiling point under reflux for 1 hour, then cooled and thereupon acidified with 5% hydrochloric acid. The mixture thus obtained is concentrated to approximately ⅓rd of its original volume by vacuum distillation. The distilland is poured into 5 volumes of water. The solvents which precipitate are isolated by filtration, dried in air, and recrystallized from aqueous methanol to give 3β,23-dihydroxy-24-norchola-5,17(20)-dien-21-oic acid γ-lactone.

EXAMPLE 3

A. A solution of 29 parts of 17-hydroxy-3-oxo-17α-pregna-4,20-diene-21-carboxylic acid γ-lactone and 5 parts of sodium cyanide in 310 parts of sulfinylbismethane is heated at the boiling point under reflux in a nitrogen atmosphere with stirring for 24 hours, whereupon the bulk of the sulfinylbismethane is removed by vacuum distillation and the distilland poured into about 375 parts of water. The resultant amber-colored solution is washed with 1,1'-oxybisethane, then distilled under reduced pressure until that portion of the 1,1'-oxybisethane wash which has dissolved therein is eliminated. The distilland is acidified with 4% hydrochloric acid. Precipitation occurs. Approximately 300 parts of water is introduced, and the resultant mixture is allowed to stand for 1 hour, then filtered. The insoluble solids thus isolated are washed with water, dried in vacuo, and recrystallized from 2-propanone to give 20-cyano-3-oxopregna-4,17(20)-diene-21-carboxylic acid as light tan prisms melting at 226°-228° (with decomposition).

B. A solution of 15 parts of 20-cyano-3-oxopregna-4,17(20)-diene-21-carboxylic acid in 500 parts of 98% formic acid is heated at the boiling point under reflux in a nitrogen atmosphere for 2 hours, then concentrated by vacuum distillation to a viscous syrup. The residue is taken up in 10 volumes of trichloromethane. The trichloromethane solution is consecutively washed with cold water and aqueous 35% sodium chloride, then dried over anhydrous sodium sulfate, and stripped of solvent by vacuum distillation. The residue is taken up in benzene; and the benzene solution is chromatographed on activated magnesium silicate, using benzene and mixtures thereof with increasing amounts of ethyl acetate as developing solvents. From an eluate comprising 5% ethyl acetate in benzene, on evaporation of solvent and crystallization of the residue from a mixture of acetone and methylcyclohexane, 3,21-dioxo-14α-carda-4,17(20)-dienolide melting at 218°–221° (with decomposition) is obtained.

C. To a solution of 5 parts of 3,21-dioxo-14α-carda-4,17(20)-dienolide in 90 parts of tetrahydrofuran is added, with stirring, a solution of 2 parts of sodium tetrahydroborate(1-) in 45 parts of tetrahydrofuran. The resultant mixture is stirred at room temperatures for approximately 4 hours, whereupon 16 parts of 15% hydrochloric acid is introduced. The mixture thus obtained is concentrated to approximately 1/5th of its original volume by vacuum distillation. The concentrate is mixed with 300 parts of trichloromethane. The mixture thus obtained is washed with aqueous 35% sodium chloride, consecutively dried over anhydrous sodium sulfate and magnesium sulfate, and stripped of solvent by vacuum distillation. The residue is 3ξ,23-dihydroxy-24-norchola-4,17(20)-dien-21-oic acid γ-lactone.

D. To a solution of 5 parts of 3ξ,23-dihydroxy-24-norchola-4,17(20)-dien-21-oic acid γ-lactone in 300 parts of trichloromethane is added 15 parts of activated manganese oxide. The resultant mixture is stirred at room temperatures for 5 hours, then filtered. The filtrate is washed with aqueous 35% sodium chloride, dried over anhydrous sodium sulfate, and stripped of solvent by vacuum distillation. The residue is 23-hydroxy-3-oxo-24-norchola-4,17(20)-dien-21-oic acid γ-lactone.

What is claimed is:

1. A compound which is 23-hydroxy-3-oxo-24-norchola-4,17(20)-dien-21-oic acid γ-lactone.

2. A compound of the formula

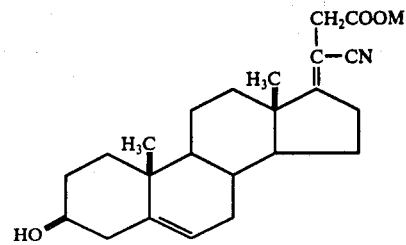

wherein M represents sodium or hydrogen.

3. A compound which is 20-cyano-3-oxopregna-4,17(20)-diene-21-carboxylic acid.

4. A compound of the formula

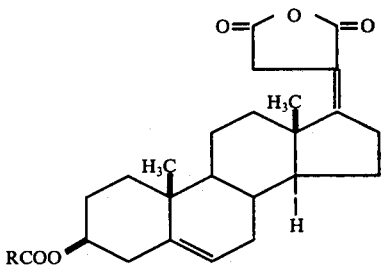

wherein R represents hydrogen or methyl.

5. A compound which is 3,21-dioxo-14α-carda-4,17(20)-dienolide.

6. A compound of the formula

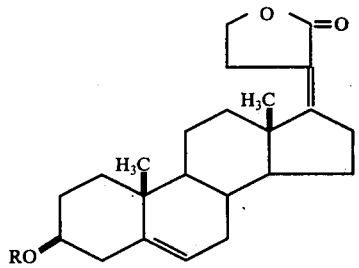

wherein R represents hydrogen or acetyl.

7. A compound which is 3ξ,23-dihydroxy-24-norchola-4,17(20)-dien-21-oic acid γ-lactone.

* * * * *